(12) United States Patent
Pulugurtha et al.

(10) Patent No.: US 11,872,359 B2
(45) Date of Patent: Jan. 16, 2024

(54) EXPANDABLE-TIP ASPIRATION GUIDE CATHETER

(71) Applicant: Covidien LP, Mansfield, MA (US)

(72) Inventors: Syamala Rani Pulugurtha, Irvine, CA (US); Maria De Jesus Sanson, Mission Viejo, CA (US)

(73) Assignee: Covidien LP, Mansfield, MA (US)

( * ) Notice: Subject to any disclaimer, the term of this patent is extended or adjusted under 35 U.S.C. 154(b) by 471 days.

(21) Appl. No.: 17/096,319

(22) Filed: Nov. 12, 2020

(65) Prior Publication Data

US 2022/0143368 A1 May 12, 2022

(51) Int. Cl.

| A61M 25/00 | (2006.01) |
| A61M 25/01 | (2006.01) |
| A61B 17/3203 | (2006.01) |
| A61B 17/12 | (2006.01) |
| A61B 17/00 | (2006.01) |

(52) U.S. Cl.
CPC .... *A61M 25/0158* (2013.01); *A61M 25/0108* (2013.01); *A61M 25/0125* (2013.01); *A61M 25/0138* (2013.01); *A61B 17/12145* (2013.01); *A61B 17/32037* (2013.01); *A61B 2017/00867* (2013.01); *A61M 25/0074* (2013.01); *A61M 25/0082* (2013.01); *A61M 2205/0266* (2013.01)

(58) Field of Classification Search
CPC .......... A61M 25/0158; A61M 25/0074; A61M 25/0082; A61M 25/0108; A61M 25/0125; A61M 25/0138; A61B 2017/00867; A61B 2017/22079; A61B 17/32037
See application file for complete search history.

(56) References Cited

U.S. PATENT DOCUMENTS

| 4,543,090 A | 9/1985 | McCoy |
| 4,601,283 A | 7/1986 | Chikama |
| 4,753,223 A | 6/1988 | Bremer |
| 5,019,040 A | 5/1991 | Itaoka et al. |
| 5,078,684 A | 1/1992 | Yasuda |
| 5,419,767 A | 5/1995 | Eggers et al. |

(Continued)

FOREIGN PATENT DOCUMENTS

| WO | 2013119425 A1 | 8/2013 |
| WO | 2018183832 A1 | 10/2018 |

(Continued)

OTHER PUBLICATIONS

"Introduction to FLEXINOL Actuator Wire," accessed from http://www.dynalloy.com/flexinol.php on or about Mar. 20, 2019, 1 pp.

(Continued)

*Primary Examiner* — Katherine H Schwiker
*Assistant Examiner* — Anna E Goldberg-Richmeier
(74) *Attorney, Agent, or Firm* — Shumaker & Sieffert, P.A.

(57) ABSTRACT

In some examples, a catheter includes an elongated body and an expandable member at a distal portion of the elongated body and defining at least part of a distal tip of the catheter. The expandable member includes a flexible membrane and an expandable ring or partial ring located at a distal portion of the expandable member, wherein the expandable ring or partial ring is configured to expand radially outward in response to electrical energy applied to the expandable ring or partial ring.

20 Claims, 6 Drawing Sheets

(56) References Cited

U.S. PATENT DOCUMENTS

| | | | |
|---|---|---|---|
| 5,531,664 A | 7/1996 | Adachi et al. | |
| 5,653,684 A | 8/1997 | Laptewicz et al. | |
| 5,662,621 A * | 9/1997 | Lafontaine | A61M 25/0041 |
| | | | 604/528 |
| 5,713,853 A * | 2/1998 | Clark | A61M 25/007 |
| | | | 604/509 |
| 5,810,717 A | 9/1998 | Maeda et al. | |
| 5,997,526 A | 12/1999 | Giba et al. | |
| 6,672,338 B1 | 1/2004 | Esashi et al. | |
| 6,872,433 B2 | 3/2005 | Seward et al. | |
| 6,936,015 B2 | 8/2005 | Esashi et al. | |
| 7,220,269 B1 | 5/2007 | Ansel et al. | |
| 7,976,460 B2 | 7/2011 | Richardson | |
| 8,343,167 B2 | 1/2013 | Henson | |
| 9,078,682 B2 | 7/2015 | Lenker et al. | |
| 9,597,171 B2 | 3/2017 | Shrivastava et al. | |
| 10,350,386 B2 | 7/2019 | di Palma et al. | |
| 10,463,351 B2 | 11/2019 | Merk et al. | |
| 10,624,659 B2 | 4/2020 | Gamba et al. | |
| 2006/0064055 A1 | 3/2006 | Pile-Spellman et al. | |
| 2007/0083084 A1 | 4/2007 | Esashi et al. | |
| 2010/0168667 A1 | 7/2010 | Kronstedt et al. | |
| 2016/0175039 A1 | 6/2016 | Aujla | |
| 2017/0136158 A1 | 5/2017 | Culhane et al. | |
| 2019/0269491 A1 * | 9/2019 | Jalgaonkar | A61M 25/0067 |
| 2019/0298396 A1 | 10/2019 | Gamba et al. | |
| 2020/0001046 A1 | 1/2020 | Yang et al. | |
| 2020/0281611 A1 * | 9/2020 | Kelly | A61B 17/221 |
| 2020/0345987 A1 | 11/2020 | Jalgaonkar et al. | |

FOREIGN PATENT DOCUMENTS

| | | |
|---|---|---|
| WO | 2019147985 A1 | 8/2019 |
| WO | 2019168737 A1 | 9/2019 |

OTHER PUBLICATIONS

"Technical Characteristics of FLEXINOL," Dynalloy, Inc., F1140RevJ, accessed from http://www.dynalloy.com on or about Mar. 20, 2019, 12 pp.

Images Scientific Instruments, "Nitinol/Flexinol Actuator Wire," accessed from https://www.imagesco.com/articles/nitinol/04.html on or about Mar. 20, 2019, 2 pp.

Komatsubara et al., "Development of the Forward-Looking Active Micro Catheter Actuated by Ti—Ni Shape Memory Alloy Springs," 2009 IEEE 22nd International Conference on Micro Electro Mechanical Systems, Jan. 25-29, 2009, IEEE, Mar. 2009, 4 pp.

Namazu et al., "Titanium-Nickel ShapeMemory Alloy Spring Actuator for Forward-Looking Active Catheter," Hindawi Publishing Corporation, Journal. of Metallurgy, vol. 2011, accepted Jan. 9, 2011, 10 pp.

International Search Report and Written Opinion of International Application No. PCT/US2021/057493, dated Mar. 11, 2022, 16 pp.

* cited by examiner

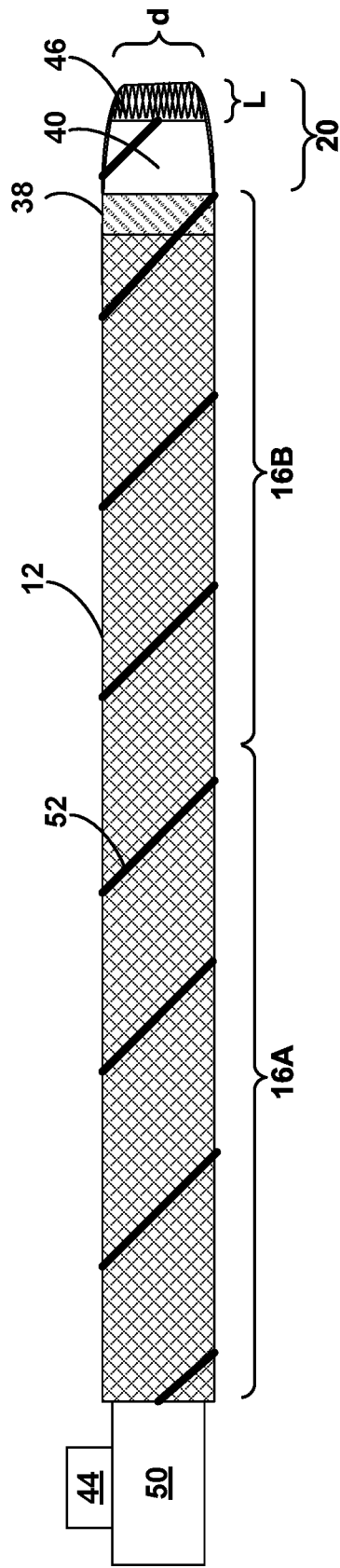
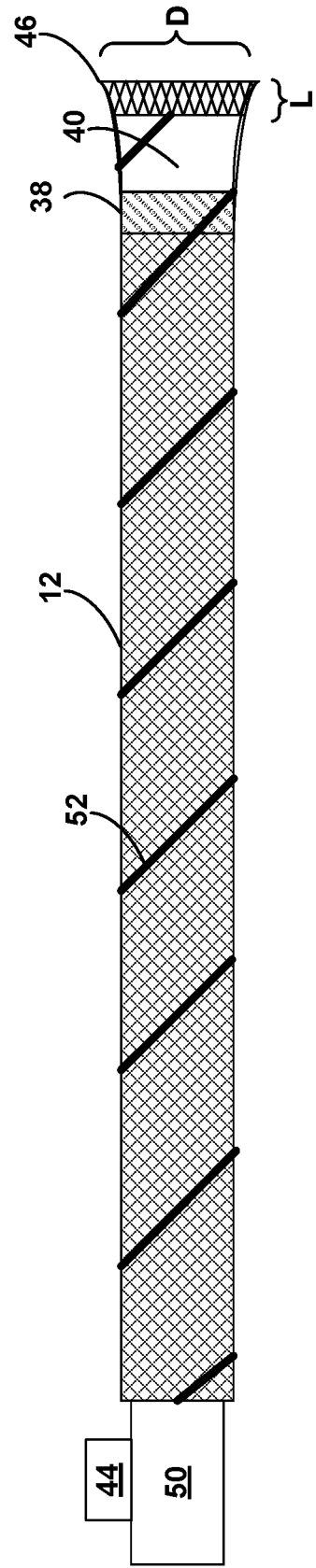
FIG. 3A
FIG. 3B

EXPANDABLE-TIP ASPIRATION GUIDE CATHETER

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

This disclosure describes example catheters including an elongated body and an expandable member at a distal portion of the elongated body and defining at least part of a distal tip of the catheter. The expandable member is configured to expand radially outward within a hollow anatomical structure (e.g., a blood vessel) of a patient, e.g., to engage a thrombus. The expandable member includes a ring-shaped structure or partial-ring-shaped structure configured to be expanded via electrically resistive heating, thereby expanding a distal mouth of the catheter. In some examples, the elongated body of the catheter includes an electrical conductor electrically connected to the ring or partial-ring structure of the expandable member. For example, the electrical conductor can be part of a structural support member of the catheter (e.g., a braid and/or a coil) or separate from the structural support member. During use, a clinician may control a device to deliver an electrical current to the expandable ring or partial-ring structure via the electrical conductor in order to resistively heat the expandable ring or partial ring structure and cause the ring or partial-ring structure to expand and expand a distal mouth of the catheter. This disclosure also describes examples of methods of forming the catheters described herein and methods of using the catheters.

Clause 1: In some examples, a catheter includes: an elongated body including a proximal body portion and a distal body portion; and an expandable member located at the distal body portion, wherein the expandable member includes: a flexible membrane; and an expandable ring or partial ring located at a distal portion of the expandable member, the expandable ring or partial ring being configured to expand radially outward in response to electrical energy applied to the expandable ring or partial ring.

Clause 2: In some examples of the catheter of clause 1, the expandable member is configured to expand radially outward from a compressed configuration to a deployed configuration in response to the electrical energy applied to the expandable ring or partial ring.

Clause 3: In some examples of the catheter of clause 1 or clause 2, the expandable ring or partial ring defines an axial length and a compressed diameter, wherein the compressed diameter is larger than the axial length.

Clause 4: In some examples of the catheter of any of clauses 1-3, the expandable ring or partial ring includes nitinol or a 50:50 nickel-titanium alloy.

Clause 5: In some examples of the catheter of any of clauses 1-4, the catheter further includes an electrical conductor extending along the elongated body, the electrical conductor configured to deliver the electrical energy from an energy source to the expandable ring or partial ring.

Clause 6: In some examples of the catheter of clause 5, the elongated body includes a braided structural support member, and the electrical conductor is woven into the braided structural support member.

Clause 7: In some examples of the catheter of clause 5, the elongated body includes a coiled structural support member, and the electrical conductor includes a coiled wire interleaved with the coiled structural support member.

Clause 8: In some examples of the catheter of clause 5, the elongated body includes a coiled structural support member including the electrical conductor.

Clause 9: In some examples of the catheter of any of clauses 1-8, the expandable ring or partial ring includes a nitinol frame defining a plurality of pores, wherein the expandable ring or partial ring is configured to resistively heat in response to receiving the electrical energy.

Clause 10: In some examples of the catheter of clause 9, the nitinol frame includes a plurality of interwoven nitinol wires.

Clause 11: In some examples of the catheter of any of clauses 1-10, the membrane includes a polymer fabric disposed around the expandable ring or partial ring.

Clause 12: In some examples of the catheter of clause 11, the polymer fabric includes silicone, polyethylene terephthalate (PET), or expanded polytetrafluoroethylene (e-PTFE).

Clause 13: In some examples of the catheter of any of clauses 1-12, the elongated body includes: an inner liner; a structural support member; an outer jacket; and a radiopaque marker band, wherein the structural support member is positioned between the outer jacket and the inner liner.

Clause 14: In some examples of the catheter of any of clauses 1-13, the catheter further includes an electrical switch disposed at the proximal portion of the elongated body, the electrical switch being configured to apply the electrical energy to the expandable ring or partial ring when the electrical switch is closed.

Clause 15: In some examples of the catheter of any of clauses 1-14, the expandable member defines a cylindrical tube while in a deployed configuration.

Clause 16: In some examples of the catheter of any of clauses 1-15, the expandable member tapers in a distal direction while the expandable member is in a compressed configuration.

Clause 17: In some examples of the catheter of any of clauses 1-16, the expandable ring or partial ring is disposed at a distal-most end of the expandable member.

Clause 18: In some examples, a method of aspirating a clot includes: distally advancing a catheter within a vasculature of a patient toward the clot, wherein the catheter includes an expandable member including a flexible membrane and an expandable ring or partial ring; closing an electrical switch to apply electrical energy via an electrical conductor to the expandable ring or partial ring to cause the expandable member to expand radially outward; actuating a suction force to aspirate the clot; opening the electrical switch to cause the expandable member to contract radially inward; and proximally withdrawing the catheter from the vasculature of the patient.

Clause 19: In some examples of the method of clause 18, the expandable ring or partial ring includes a nitinol frame defining a plurality of pores, and the expandable ring or partial ring is configured to resistively heat in response to receiving the electrical energy.

Clause 20: In some examples, a system includes: an energy source; and a catheter including: an elongated body including a proximal body portion and a distal body portion;

and an expandable member located at the distal body portion, wherein the expandable member is configured to expand radially outward, and wherein the expandable member includes: a flexible membrane; and an expandable ring or partial ring located at a distal portion of the expandable member, the expandable ring or partial ring being configured to expand radially outward in response to electrical energy applied from the energy source to the expandable ring or partial ring.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIGS. 3A and 3B are conceptual side views of another example of the catheter of FIG. 1 with the expandable member in a contracted configuration and an expanded configuration, respectively.

DETAILED DESCRIPTION

Figure 1:
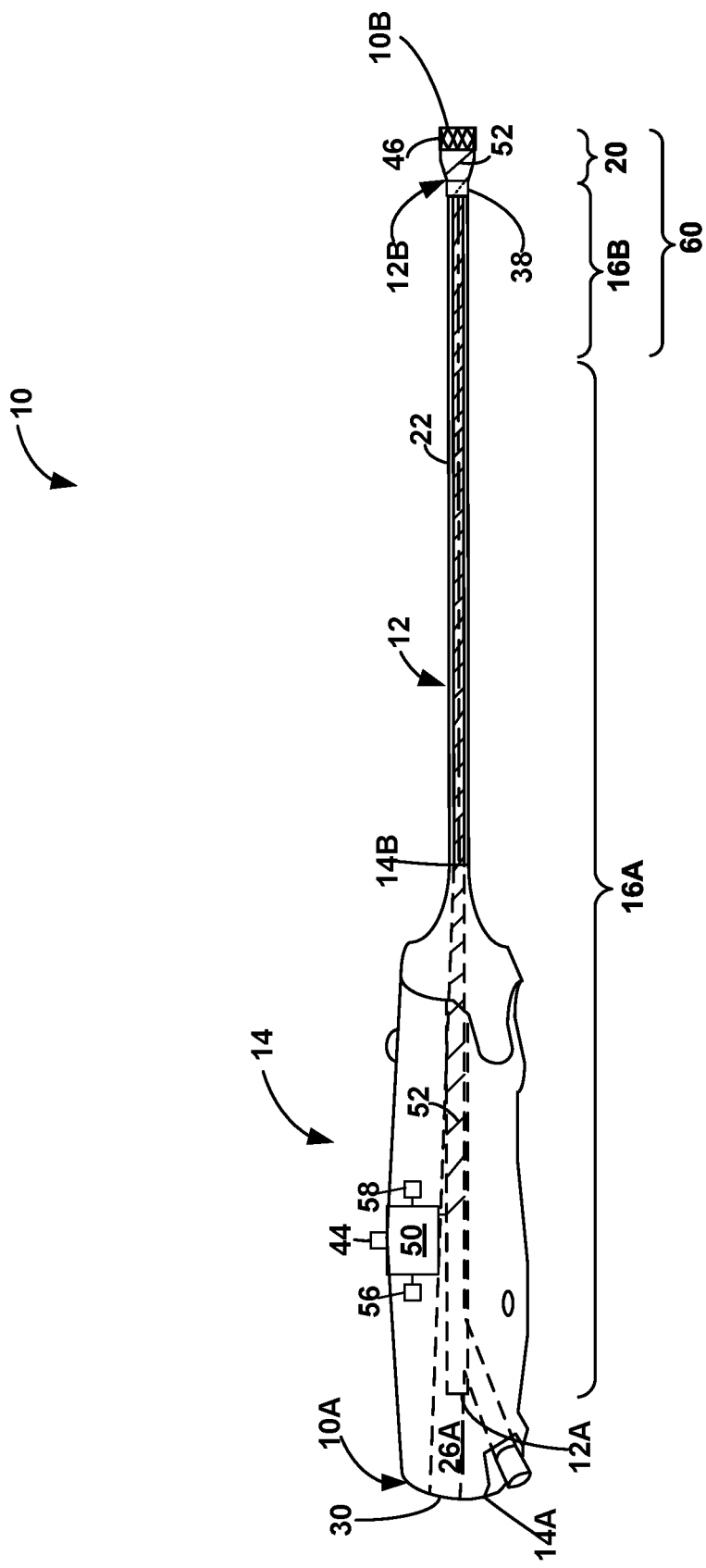
FIG. 1 is a conceptual side view of an example catheter, which includes an elongated body and an expandable member at a distal portion of the elongated body.

The disclosure describes a medical device, referred to herein as a catheter, including an expandable member configured to expand radially outward within a hollow anatomical structure (e.g., a blood vessel) of a patient, e.g., to engage with a thrombus, such as to facilitate aspiration of the thrombus (or other material or object(s) to be removed, such as a plaque or foreign body). In examples described herein, the expandable member includes a ring-shaped or partial-ring-shaped structure configured to be actuated (e.g., expanded) by electrically resistive heating, thereby expanding a distal mouth of the catheter in order to better engage the thrombus.

Example catheters described herein include a relatively flexible elongated body configured to be navigated through vasculature of a patient, e.g., tortuous vasculature in a brain of the patient. The elongated body may include a plurality of concentric layers, such as an inner liner, an outer jacket, and a structural support member (e.g., a coil, braid, and/or hypotube) positioned between at least a portion of the inner liner and outer jacket. A distal portion (e.g., a distal tip) of the catheter includes an expandable member configured to expand radially outward in response to an applied electrical current passing through a relatively electrically resistive material of the expandable member. This may enable, for example, the expandable member to engage with a thrombus, such as a clot, embolism, or other material such as plaques or foreign bodies during an aspiration procedure, such as, but not limited to, a medical procedure using A Direct Aspiration first Pass Technique (ADAPT) for acute stroke thrombectomy. In some examples, the expandable member is distinct from, but mechanically coupled to, the distal portion of the elongated body. In other examples, the expandable member is integrally formed with (e.g., laminated with and/or forming a distal extension of) the distal portion of the elongated body.

The expandable member includes a ring-shaped structure or partial-ring-shaped structure configured to be expanded via electrically resistive heating, thereby expanding a distal mouth of the catheter. The catheter includes an electrical conductor electrically connected to the ring or partial-ring structure of the expandable member and configured to electrically connect the ring or partial-ring structure to a source of electrical current. For example, the electrical conductor can be part of (e.g., integrated into) the structural support member of the elongated body and/or a structural frame of the expandable member. The structural frame is different from the expandable ring-shaped structure or partial-ring-shaped structure. In other examples, the electrical conductor can be separate from the structural support member and/or a structural frame of the expandable member. During use, a clinician may control a device to deliver an electrical current to the expandable ring or partial-ring structure via the electrical conductor in order to resistively heat the expandable ring or partial-ring structure and cause the ring or partial ring structure to expand and expand a distal mouth of the catheter.

The expandable member may help improve aspiration of the thrombus into the catheter by providing a relatively large luminal diameter (and therefore exert a larger aspiration force against the thrombus or other material to be removed) and interior space for the thrombus to engage with the catheter compared to examples in which an otherwise similar catheter does not include an expandable member. For example, such a catheter that does not include an expandable member may have limited radial expansion due to a structural support member that extends to the distal end of the catheter, and may thus make it harder to aspirate a thrombus (e.g., due to a smaller cross-sectional dimension of the distal end of the catheter). The expandable member may overcome such radial expansion limitations, thereby increasing thrombus engagement, reducing the amount of time required for revascularization, and increasing revascularization success rates for various procedures, as compared to similar procedures performed using catheters that do not include an expandable member to engage a thrombus.

Figure 2:
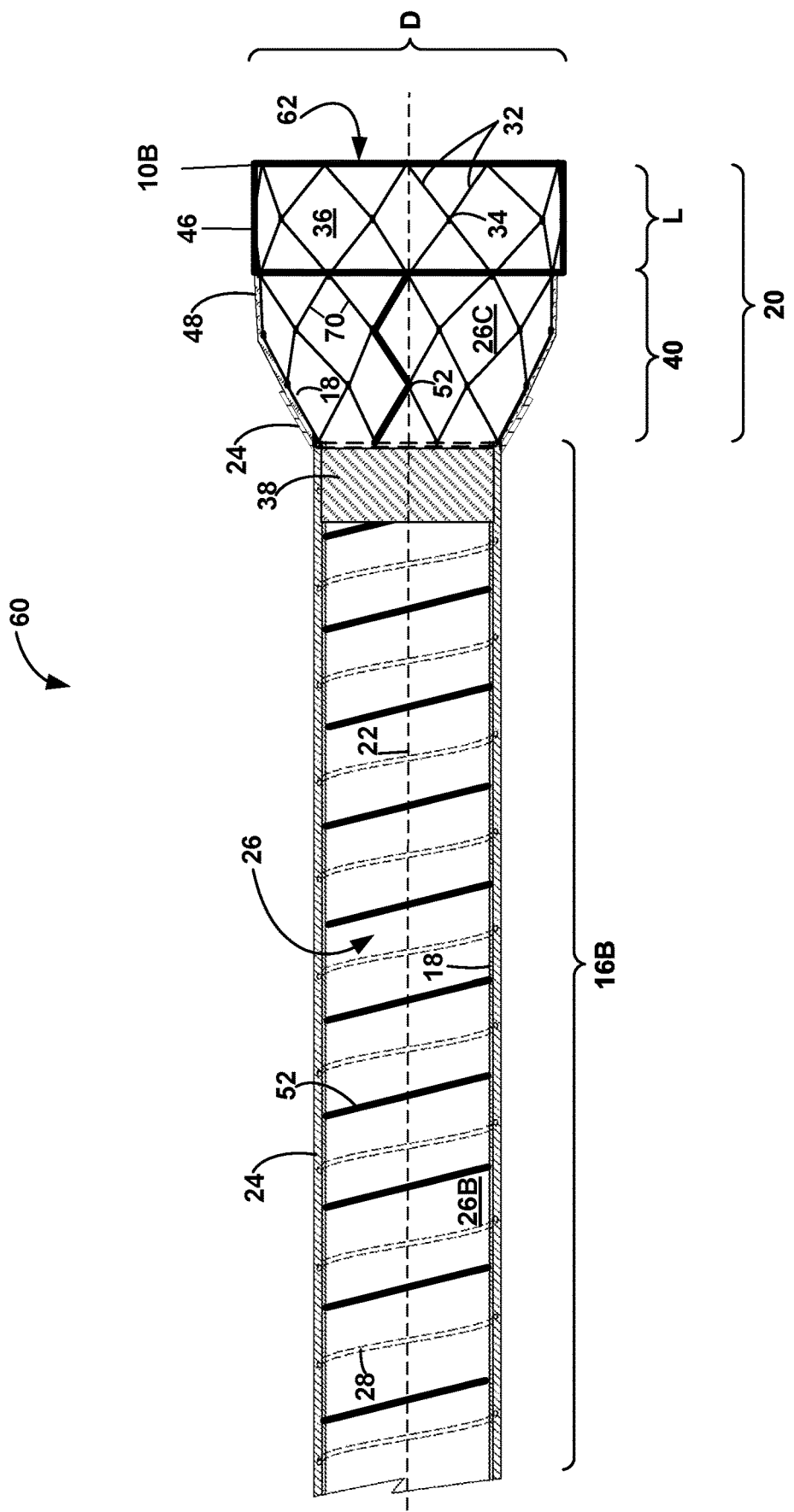
FIG. 2 is a conceptual cross-sectional view of an example of the distal tip of the catheter of FIG. 1, including the distal portion of the elongated body and the expandable member, where the cross-section is taken through a center of the catheter and along a longitudinal axis.

FIG. 1 is a conceptual side view of an example catheter 10, and FIG. 2 is a conceptual cross-sectional view of a distal portion 60 of the example catheter 10, where the cross-section is taken through a center of catheter 10 and along longitudinal axis 22 of catheter 10. The distal portion 60 can be, for example, a distal-most tip of catheter 10. As shown in FIGS. 1 and 2, catheter 10 can include an elongated body 12, a handle 14, and an expandable member 20. Catheter 10 defines at least one inner lumen, shown as inner lumen 26, including a handle lumen 26A, a body lumen 26B, and an expandable member lumen 26C.

Elongated body 12 is configured to be advanced through vasculature of a patient via a pushing force applied to proximal body portion 16A (e.g., via handle 14) of elongated body 12 without buckling, kinking, or otherwise undesirably deforming (e.g., ovalization). As shown in FIG. 2, elongated body 12 can include a plurality of concentric layers, such as an inner liner 18, an outer jacket 24, and a structural support member 28 positioned between at least a portion of inner liner 18 and at least a portion of outer jacket 24. Elongated body 12 includes a proximal body portion 16A and a distal body portion 16B, which are each longitudinal sections of elongated body 12 and do not overlap in the longitudinal direction (along longitudinal axis 22). Elongated body 12 extends from body proximal end 12A to body distal end 12B and defines at least one body lumen 26B. In the example shown in FIG. 1, proximal end 12A of elongated body 12 is received within handle 14 and is mechanically connected to handle 14 via an adhesive, welding, or another suitable technique or combination of techniques. Inner lumen 26 of catheter 10 may be defined by portions of handle 14, inner liner 18, and expandable member 20.

Catheter 10 may be used as an aspiration catheter to remove a thrombus or other material such as plaques or foreign bodies from vasculature of a patient. In such examples, a suction force (e.g., a vacuum) may be applied to proximal end 10A of catheter 10 (e.g., via handle 14) to draw a thrombus or other blockage into inner lumen 26. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, catheter 10 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Elongated body 12 may be structurally configured to be relatively flexible, pushable, and relatively kink- and buckle-resistant, so that it may resist buckling when a pushing force is applied to a relatively proximal section of catheter 10 (e.g., via handle 14) to advance elongated body 12 distally through vasculature, and so that it may resist kinking when traversing around a tight turn in the vasculature. In some examples, elongated body 12 is configured to substantially conform to the curvature of the vasculature. In addition, in some examples, elongated body 12 has a column strength and flexibility that allow at least distal body portion 16B of elongated body 12 to be navigated from a femoral artery, through the aorta of the patient, and into the intracranial vascular system of the patient, e.g., to reach a relatively distal treatment site.

Although primarily described as being used to reach relatively distal vasculature sites, catheter 10 may also be configured to be used with other target tissue sites. For example, catheter 10 may be used to access tissue sites throughout the coronary and peripheral vasculature, the gastrointestinal tract, the urethra, ureters, fallopian tubes, veins and other body lumens.

In some examples, a "working length" of catheter 10 may be measured from distal end 14B of handle 14 to distal end 10B of catheter 10 along longitudinal axis 22. The working length of catheter 10 may depend on the location of the target tissue site within the body of a patient or may depend on the medical procedure for which catheter 10 is used. For example, if catheter 10 is a distal access catheter used to access vasculature in a brain of a patient from a femoral artery access point at the groin of the patient, catheter 10 may have a working length of about 115 centimeters (cm) to about 145 cm or more, such as about 130 cm, although other lengths may be used. Distal portion 60 of catheter 10, including distal body portion 16B of elongated body 12 and expandable member 20, may be about 5 cm to about 35 cm in length. Proximal body portion 16A of elongated body 12 may be about 90 cm to about 130 cm in length, depending on the length of distal portion 60. In other examples, such as examples in which catheter 10 is a distal access catheter used to access vasculature in a brain of a patient from a radial artery access point, catheter 10 may have a working length of about 80 cm to about 120 cm, such as about 85 cm, 90 cm, 95 cm, 100 cm, or 105 cm, although other lengths may be used (e.g., sheaths or radial intermediate catheters may be 5-8 cm longer).

Expandable member 20 is configured to radially expand within a vessel of a patient, e.g., to engage a thrombus within the vessel. Expandable member 20 is positioned at (e.g., overlapping with or entirely distal to) distal body portion 16B of elongated body 12, such that a distal end of expandable member 20 defines distal end 10B of catheter 10 and a distal mouth 62 open to inner lumen 26 of catheter 10. For example, expandable member lumen 26C may form a distal extension of the internal lumen 26B of the elongated body 12.

Expandable member 20 includes a partially or completely circumferential structure, or a ring-like structure or partial-ring-like structure 46 (referred to herein as "ring 46") configured to expand radially outward, thereby expanding lumen 26C radially outward. For example, ring 46 may include a structure defining a full circumference of a circle or a majority of the circumference of a circle, as viewed along longitudinal axis 22. In other examples, ring 46 may include other geometric shapes that are non-circular in cross-section. As one non-limiting example, ring 46 may include a structure having a pleated-ring shape (e.g., as shown in FIG. 4C) or a flower-petal shape (e.g., as shown in FIG. 4D), wherein an outer surface of ring 46 varies in radius (relative to longitudinal axis 22), or in other words, ring 46 folds radially inward on itself at a plurality of points around its circumference while expandable member 20 is in a contracted configuration. As described further below with respect to FIGS. 4A-4D, ring 46 can include any suitable outer shape, including an undulating (e.g., sinusoidal or zig-zagging straight lines).

In some examples, ring 46 is characterized by its relative dimensions, in that its outer diameter D (e.g., the cross-sectional width as measured transverse to longitudinal axis 22) is always (in such examples) longer than its axial length L (as measured parallel to longitudinal axis 22), regardless of whether ring 46 is in a contracted configuration (e.g., FIG. 3A) or an expanded configuration (e.g., FIG. 3B).

In the example illustrated in FIG. 2, ring 46 (e.g., a distal-most section of expandable member 20), when in the expanded state (FIG. 3B), has a larger inner diameter and outer diameter than distal portion 16B of elongated body 12. Ring 46 can be configured to be generally cylindrical, with a constant or substantially constant inner diameter and/or outer diameter along its length. In some examples, the axial length of ring 46 can be 3 millimeters (mm) to about 5 mm, to facilitate engulfing a thrombus during use.

Ring 46 includes an electrically resistive, shape-memory material and is configured to expand in response to an application of an electrical energy. For example, expandable ring 46 may be formed from a material or metal that is configured to bend or deflect in response to a current passed therethrough (or to heat generated as a result of such current). One such type of material is shape-memory alloy actuator material, e.g. nitinol or a Ni:Ti composition of about 50:50 (e.g., Flexinol™ available from Dynalloy, Inc. of Irvine, California).

In some examples, expandable ring 46 comprises one or more materials that resistively heat in response to an electrical signal delivered via an electrical conductor 52 electrically connected to ring 46. For example, ring 46 may be formed from materials having a relatively high electrical resistivity, such that a relatively large amount of heat is generated by ring 46 for a particular level of current delivered via electrical conductor 52. In some examples, one or more materials of ring 46 (and/or ring 46 as a whole) has an electrical resistivity greater than about 30 microohms·centimeter (μΩ·cm) at room temperature. For example, the above-mentioned nickel titanium alloys, such as nitinol and a Ni:Ti composition of about 50:50 (e.g., Flexinol™), are examples of thermoactive materials that may have a desired resistivity specification.

In some examples, ring 46 may include one or more materials comprising electroactive elements ("electroactive materials"), such as materials having a high electroactive effect. An electroactive material may be any material that directly converts electrical potential (and/or current) into a substantial temperature difference. An electroactive material may be selected for a variety of properties including, but not limited to, high electrical conductivity, high Seebeck coefficient, low thermal conductivity, and other properties related to electroactive effects (e.g., Seebeck effect, Peltier effect, etc.) of materials.

In some examples, the inside and/or outside diameter of ring 46 (in the expanded state) can be established by heat-setting ring 46 on a generally cylindrical mandrel having a mandrel diameter approximately equal to the desired expanded-state inside diameter of ring 46. In this manner, the expanded-state inside and/or outside diameter of distal section 20C can be selected to enable ring 46 to provide a large distal mouth 62 for application of high suction force to a thrombus or other material to be aspirated. In some examples, the expanded-state outside diameter of ring 46 can be about 150 percent to about 300 percent of the outside diameter of distal portion 16B of elongated body 12. In some examples, the expanded-state outer diameter of ring 46 can be about 150 percent, 200 percent, 250 percent, or 300 percent of the outside diameter of distal portion 16B of elongated body 12 (or of the outside diameter of the proximal end of expandable member 20). In some examples, an outer diameter of ring 46 is no more than 300 percent of the outer diameter of the distal body portion 16B.

In some examples, the axial length of expandable member 20 (as measured along longitudinal axis 22) is defined by the axial length L of ring 46. In other examples, such as the examples shown in FIGS. 1 and 2, ring 46 is disposed at a distal-most end of expandable member 20, and expandable member 20 also includes an expandable member proximal section 40 that does not include ring 46 and is proximal to ring 46. In some such examples, ring 46 is the portion of expandable member 20 that is electrically coupled to an electrical conductor 52 (e.g., a conductive wire) and configured to resistively heat in order to expand radially outward, and proximal section 40 is not electrically connected to electrical conductor 52. In some such examples, but not all such examples, ring 46 may be mechanically coupled to, but electrically insulated from, proximal section 40.

In some examples, such as the example shown in FIG. 2, proximal section 40 of expandable member 20 includes a flexible membrane 48 and a structural frame 70, such as a metal frame 70. For example, the metal frame 70 may include a coiled structure, a braided structure, a woven structure, and/or a laser-cut-stent-like structure. In some such examples, the structural frame 70 of proximal section 40 may be a distal extension of structural support member 28 of elongated body 12. In other examples, however, structural frame 70 of proximal section 40 may be separate from structural support member 28. The structural frame 70 of proximal section 40 may be mechanically coupled to ring 46 so as to at least partially expand in response to receiving an expansion force from ring 46 as ring 46 expands in response to an applied electrical current and/or potential, but the structural frame 70 of proximal section 40 may not itself be conductively coupled to an electrical conductor 52. In some such examples, due to the expandable construction of structural frame 70, expandable member 20 may form a generally cylindrical shape rather than a funnel shape when expandable member 20 is in an expanded configuration.

In other examples, such as the example shown in FIG. 1, proximal section 40 of expandable member 20 may include a flexible membrane 48 with no structural frame. In any of these examples, flexible membrane 48 may be at least partially coupled to (e.g., radially inward and/or radially outward of) the expandable ring 46, covering expandable ring 46, and/or integrated into the expandable ring 46. In some examples, flexible membrane 48 may include an elastomeric material, such as a polymer fabric. For example a polymer fabric may include as silicone, polyethylene terephthalate (PET), expanded polytetrafluoroethylene (e-PTFE), polyolefin thermoplastic elastomers, polyurethane elastomeric alloys, silicone, or any other suitable material that permits the radially outward expansion of expandable member 20.

In some examples, in its expanded state, expandable member 20 defines a tubular, cylindrical, or funnel shape configured to provide catheter 10 with a relatively large diameter (or other maximum cross-sectional diameter) distal end 10B (compared to, for example, proximal body portion 16A of elongated body 12) and interior space 26C for better engagement with a thrombus (e.g., clot or embolus). In some examples, the cross-section of expandable member 20 in its expanded state may be round (e.g., circular) and the cross-sectional axis may be referred to as a diameter. In some examples, the cross-section may be irregularly shaped, in which case the cross-sectional dimension may be referred to as the major axis (e.g., a longest dimension of the cross-section). In the expanded configuration, the cross-section of expandable member 20 may be wider at a distal end than a proximal end. For example, in the expanded configuration, the inner diameter at the distal end of expandable member 20 (e.g., along all or part of distal section 20C of expandable member (FIG. 3) and/or at distal opening 62) may be about 150 percent to about 300 percent wider than an inner diameter of expandable member 20 near distal body portion 16B of elongated body 12.

Expandable member 20, including structural frame 70 of proximal section 40 if present, may include an expandable stent-like structure (e.g. a laser-cut tubular structure having a number of struts) or an expandable braid or weave, which can each be formed from a plurality of interwoven structural elements, such as braided round wires. In some examples, such as the examples shown in FIG. 2, structural frame 70 of expandable member 20 may resemble a stent-like structure that includes a tubular body comprising a plurality of struts 32 (e.g., an individual straight portion of an undulating ring) that are interconnected via one or more connections at adjacent vertices 34 (peaks or valleys) to define a plurality of pores or cells 36 between adjacent struts 32, such as diamond-shape cells or other cell designs. In general, each of the struts 32 of expandable member 20 may be a substantially straight portion (e.g., a straight or nearly straight member) that may join with one or more other struts 32 at a respective vertex 34. Struts 32 may be forced apart and radially outward from one another (e.g., via straightening of the undulating rings) to increase the diameter at various portions of expandable member 20. In other examples, expandable member 20 may include an expandable braid, an expandable mesh (e.g., woven sleeve or woven tubular structure), or other design.

Expandable member 20 can be configured to facilitate thrombus removal. In examples in which catheter 10 is used with an aspiration procedure (e.g., ADAPT technique), the size and shape of expandable member 20 may enable catheter 10 to better engage a thrombus by increasing the distal opening 62 into which the thrombus may be received, increasing the total aspiration force exerted on the thrombus via a larger luminal area, and/or by distributing the aspiration forces over a greater portion of the thrombus rather than a localized area, thereby allowing the thrombus to be aspirated into catheter 10 more effectively. Expandable member 20 enables catheter 10 to maintain a relatively small diameter elongated body 12 (e.g., within proximal body portion 16A) to facilitate navigability of catheter 10, while also enabling catheter 10 to exhibit improved engagement and suction force characteristics that may be attributed to having a large-diameter distal end 10B. In some examples, the presence of expandable member 20 may lead to improved revascularization success rates, such as due to the improved thrombus engagement and/or suction (e.g., to better pull the entirety of the thrombus into catheter 10 during aspiration) as described herein.

Expandable member 20 may be of any suitable length and diameter, which may be selected based on the target vessel or particular procedure being performed. For example, expandable member 20 may be made be long enough to fully engulf a thrombus (e.g., an average amount of thrombus material), but short enough to avoid excessive friction between an outer surface of expandable member 20 and an inner surface of an introducer sheath or an outer catheter. In some examples, expandable member 20 may be about 2 centimeters to about 25 centimeters long, measured in a direction parallel to longitudinal axis 22. For example, expandable member 20 may be about 1.5 cm, about 2.0 cm, or about 25 cm in length, such as from about 0.5 cm to about 3.0 cm.

As discussed above, in some examples, in the collapsed state (FIG. 3A), a distal section of expandable member 20 may have a cross-sectional dimension substantially equal to (e.g., equal to or nearly equal to) or less than the outer diameter of elongated body 12 proximate to expandable member 20. In some examples in which expandable member 20 defines a tube shape or a cylinder shape (having an open distal mouth 62) in an expanded state, expandable member 20 may define a substantially constant diameter (e.g., constant or nearly constant in the absence of forces compressing expandable member 20) along about 0.5 cm to about 3 cm, or 0.5 cm to about 2.5 cm of a length of expandable member 20, which can be a distal-most length in some examples.

In some examples, in the expanded configuration (FIG. 3B), diameter D at distal end 10B of expandable member 20 may be about 150 percent to about 300 percent of the diameter of the proximal end of expandable member 20. In some examples, the expanded outer diameter or the cross-sectional dimension D of expandable member 20 at distal end 10B may be about 200 percent, 250 percent, 300 percent, or another larger percentage of the outer diameter or cross-sectional dimension of a portion of elongated body 12.

In some examples, an inner surface of expandable member 20 may comprise a surface treatment configured to promote at least one of mechanical or chemical engagement between the inner surface and the thrombus, and enable the thrombus to be pulled into lumen 26 of catheter 10 more effectively. For example, a coating may be applied to portions of the inner surface of expandable member 20 (e.g., the inner surface of the struts or braided filaments, or a flexible membrane 48 if present), where the coating has a relatively high clot affinity. Such affinity may be measured, for example, with a dynamic mechanical analyzer (DMA) equipped with a shear sandwich clamp. Examples of suitable coating materials to increase the affinity of the thrombus to expandable member 20 may include, for example, a thermoplastic elastomer such as ChronoPrene™ (AdvanSource Biomaterials, Wilmington, Massachusetts), ChronoPrene™ (AdvanSource Biomaterials, Wilmington, Massachusetts), ChronoPrene™ 5A, ChronoPrene™ 15A; a polyolefin elastomer such as ethylene-octene or ethylene-butene copolymer, for example, ENGAGE™ Polyolefin Elastomers (Dow Chemical Company, Midland, Michigan), ENGAGE™ 8107, 7367, 7270; or the like.

As another example, portions of the inner surface of expandable member 20 may be textured via etching or otherwise roughened (or rougher) in comparison to the outer surface of the expandable member 20 to better mechanically engage the thrombus. In some examples, an inner surface of expandable member 20 can include a polymer that is etched to promote mechanical thrombus engagement.

In some examples, thrombus engagement with expandable member 20 may be enhanced by delivering electrical energy to expandable member 20. The electrical energy may be the same as, or different from, the electrical current used to cause ring 46 to resistively heat and expand. For example, a source of electrical energy 50 (e.g., an electrical signal generator) may deliver an electrical signal to expandable member 20 via one or more electrical conductors (not shown) electrically coupled to expandable member 20. The electrical energy may be positively charged to electrostatically engage a thrombus. Characteristics of the electrical energy may be adjusted to better engage the thrombus, such as polarity, or an amount or type of current delivered. For example, pulsed direct current may be employed, optionally with a non-square and/or non-negative waveform. The electrical conductors can extend through inner lumen 26B of elongated body 12, can extend along an outer surface of elongated body 12, can be embedded in a wall of elongated body 12, or have any other suitable configuration.

Handle 14 may be positioned at (e.g., proximal to or at least partially overlapping with) a proximal body portion 16A of elongated body 12. Proximal end 14A of handle 14 may define the catheter proximal end 10A of catheter 10 and may include an opening 30 aligned with inner lumen 26B of elongated body 12, such that inner lumen 26B of elongated body 12 may be accessed via opening 30 and, in some examples, closed via opening 30. In some examples, handle 14 may include a luer connector, a hemostasis valve, or another mechanism or combination of mechanisms for connecting handle 14 to another device such as a vacuum source for performing the aspiration techniques described herein. In some examples, proximal end 10A of catheter 10 can include another structure in addition to, or instead of, handle 14, such as a catheter hub.

As shown in FIG. 1, handle 14 may include an electrical switch 44, an electrical power source 50, control circuitry 56, and electrical generating circuitry 58. In other examples, any or all of these components may be located elsewhere within catheter 10, or external to catheter 10, e.g., as part of a separate medical device electrically connected to electrical conductor 52 of catheter 10. Electrical switch 44 enables a user to control an expansion and contraction of expandable member 20 by closing and opening the switch, respectively. Control circuitry 56 provides intermediate functionality between switch 44 and expandable member 20, e.g., receives user input via switch 44 and causes expandable member 20 to expand in response to the user input. Electrical power source 50, such as a battery or other power source, provides the energy that enables expandable member 20 to expand in response to user input. Electrical generating circuitry 58 provides intermediate functionality between electrical power source 50 and expandable member 20, e.g., converts raw electrical power from power source 50 into an electrical signal having suitable parameters (e.g., voltage, current, frequency, etc.) to cause expandable member 20 to expand.

Electrical switch 44 includes a user input mechanism, such as a button, lever, dial, slider, lever, or the like or combination thereof, configured to enable a user to close and open the switch to complete and disconnect an electrical circuit, respectively. Electrical power source 50 may include a battery, capacitor, or a wired or wireless connection to an active power source, such as an electrical outlet. Control circuitry 56 and electrical generating circuitry 58 include any circuitry coupled to switch 44 (and/or other user input, if present) and power source 50, and configured to enable the functionality of catheter 10 as described herein, such as the expansion capabilities of ring 46. For example, control circuitry 56 and/or electrical generating circuitry 58 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 56 and/or electrical generating circuitry 58 may include multiple components, such as any combination of one or more microprocessors, one or more DSPs, one or more ASICs, or one or more FPGAs, as well as other discrete or integrated logic circuitry, and/or analog circuitry.

In some examples, inner liner 18 of elongated body 12 defines at least a portion 26B of inner lumen 26 of catheter 10, inner lumen 26B defining a passageway through elongated body 12. In some examples, inner lumen 26B may extend over the entire length of inner liner 18 (e.g., from proximal end 12A of elongated body 12 to the distal end 12B). Inner lumen 26B may be sized to receive a medical device (e.g., another catheter, a guidewire, an embolic protection device, a stent, or any combination thereof), a therapeutic agent, or the like. Elongated body 12, alone or with inner liner 18 and/or other structures, may define a single inner lumen 26, or multiple inner lumens (e.g., two inner lumens or three inner lumens 26A-26C) of catheter 10.

Inner liner 18 may be formed using any suitable material, such as, but not limited to, polytetrafluoroethylene (PTFE), expanded PTFE (ePTFE, e.g., unidirectional ePTFE or bi-directional ePTFE), a fluoropolymer, perfluoroalkoxy alkane (PFA), fluorinated ethylene propylene (FEP), polyolefin elastomers or any combination thereof. A unidirectional ePTFE may be stretched in one of the longitudinal or radial directions, and a bi-directional ePTFE may be stretched in both the longitudinal and radial directions. Other examples of materials from which inner liner 18 may be formed include, but are not limited to, Low Density Polyethylene (LDPE) (e.g., about 42D), a PTFE having a durometer of about 60D, High Density Polyethylene (HDPE), or any combination thereof. Some such polyolefin materials may have similar coefficients of friction as PTFE and may be conducive to processing.

Elongated body 12 includes one or more structural support members 28 positioned over inner liner 18. Structural support member 28 is configured to increase the structural integrity of elongated body 12 while allowing elongated body 12 to remain relatively flexible. For example, structural support member 28 may be configured to help elongated body 12 substantially maintain its cross-sectional shape (e.g., circular or nearly circular) or at least help prevent elongated body 12 from buckling or kinking as it is navigated through tortuous anatomy. Additionally, or alternatively, structural support member 28, together with inner liner 18, and outer jacket 24, may help distribute both pushing and rotational forces along a length of elongated body 12, which may help prevent kinking of elongated body 12 upon rotation of body 12 or help prevent buckling of body 12 upon application of a pushing force to body 12. As a result, a clinician may apply pushing forces, rotational forces, or both, to the proximal portion of elongated body 12, and such forces may cause a distal portion of elongated body 12 to advance distally, rotate, or both, respectively.

Structural support member 28 may include one or more tubular braided structures, one or more coil members defining a plurality of turns, e.g., in the shape of a helix, one or more hypotubes, or a combination of one or more braided structures, one or more coil members, and/or one or more hypotubes. Thus, although the examples of the disclosure primarily describe structural support member 28 as a coil, in other examples, catheter 10 may include a braided structure instead of a coil, a braided structure in addition to a coil, or a combination that includes one or more of each structure. As one example, a proximal portion of structural support member 28 may include a braided structure and a distal portion of structural support member 28 may include a coil member. As another example, elongated body 12 can include a coil radially inward and/or radially outward of a braid.

Structural support member 28 can be made from any suitable material, such as, but not limited to, a metal (e.g., a nickel titanium alloy (nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 28 may include one or more metal wires braided or coiled around inner liner 18. The metal wires may include round wires, flat-round wires, flat wires, or any combination thereof.

Structural support member 28 may extend along only a portion of a length of elongated body 12 and is positioned proximal to expandable member 20. In some examples, the distal end of structural support member 28 may abut the proximal end of expandable member 20 and may be coupled to expandable member 20 (e.g., mechanically coupled or bonded with adhesive, or welded). In other examples, expandable member 20 may not be coupled to structural support member 28 or may not be in direct contact (e.g., abutting contact) with structural support member 28, although the two members may be in the same radial layer of elongated body 12 (and/or have the same inner diameter and/or outer diameter where structural support member 28 and expandable member 20 meet or come closest to each other in the longitudinal direction). For example, the distal end of structural support member 28 may be adjacent to the proximal end of expandable member 20 but separated by a small gap. In such examples, structural support member 28 and expandable member 20 may be in the same radial layer and inner liner 18, outer jacket 24, or both may secure both expandable member 20 and structural support member 28 in place along elongated body 12.

In some examples, structural support member 28 may be coupled, adhered, or mechanically connected to at least a portion of an outer surface of inner liner 18. For example, structural support member 28 may be positioned over inner liner 18 and secured in place (e.g., fixed) relative to inner liner 18 by outer jacket 24 using a melt-reflow/heat shrink process, via adhesives or other suitable technique.

Elongated body 12 can also include outer jacket 24 positioned over structural support member 28 and inner liner 18, the structural support member 28 being positioned between portions of inner liner 18 and outer jacket 24. In some examples, outer jacket 24 may be positioned around structural support member 28 such that outer jacket 24 covers at least a part or all of both inner liner 18 and structural support member 28. Outer jacket 24, together with inner liner 18 and structural support member 28, may be configured to define elongated body 12 having the desired structural characteristics (e.g., flexibility, kink resistance, torque responsiveness, structural integrity, pushability, and column strength, which may be a measure of a maximum compressive load that can be applied to elongated body 12 without taking a permanent set). For example, outer jacket 24 may have stiffness characteristics that contribute to the desired stiffness profile of elongated body 12.

In some examples, outer jacket 24 may be formed using any suitable material including, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer (e.g., a thermoplastic, elastomeric polymer configured to accommodate radial expansion of expandable member 20), polyurethanes, polyamides, or other thermoplastic material, or combinations thereof.

Outer jacket 24 may be heat shrunk around structural support member 28 and, in some examples, at least a portion (e.g., proximal section 40) of expandable member 20 to secure the two members 20, 28 in the same radial layer. In some examples, during the heat shrinking of outer jacket 24 around structural support member 28, the material of outer jacket 24 may flow into at least some of the inner spacings or gaps (e.g., gaps between the adjacent turns of the coils, or between the struts or braids) within structural support member 28 or expandable member 20 such that portions of outer jacket 24, structural support member 28, and/or expandable member 20 form a laminated structure.

In some examples, at least a portion of an outer surface of outer jacket 24 and/or expandable member 20 includes one or more coatings, such as, but not limited to, an anti-thrombogenic coating, which may help reduce the formation of thrombi in vitro, an anti-microbial coating, and/or a lubricating coating.

In some examples, a portion of expandable member 20 may be mechanically coupled to structural support member 28 and/or layered between inner liner 18 and outer jacket 24. For example, in examples in which expandable member proximal section 40 includes a structural frame 70, proximal section 40 and structural support member 28 can be formed independently of one another, and the proximal end of the structural frame 70 of proximal section 40 may be mechanically coupled to the distal end of structural support member 28. In some examples, the structural frame of proximal section 40 and structural support member 28 may be joined via welding, brazing, soldering, adhesives, epoxy, or other suitable technique. In some examples, structural frame 70 may be welded, soldered, bonded, or hooked to structural support member 28.

In some examples, structural frame 70 of expandable member 20 comprises a plurality of struts 32 that define a plurality of cells 36. One or more of the proximal peaks of the proximal-most strut (e.g., at the proximal end of expandable member 20) may be coupled to structural support member 28 such that expandable member 20 is mechanically coupled to structural support member 28 at a plurality of circumferential positions around structural support member 28, such as shown in FIG. 2. In some examples, structural frame 70 may be bonded (e.g., glued), hooked (e.g., mechanically interlocked), or coupled to structural support member 28 using other means.

In some examples, structural support member 28 and a structural frame 70 may be integrally formed. For example, structural support member 28 may include a plurality of wires (e.g., coils or braids) that are subsequently woven to form structural frame 70 of expandable member 20. In other examples, structural support member 28 and structural frame 70 may be formed using the same hypotube; the proximal portion of the hypotube being spirally cut to form a somewhat coil-like structure (e.g. structural support member 28) while the distal portion of the hypotube is cut to form a plurality of interconnected struts that form structural frame 70.

Additionally, or alternatively, expandable member 20 may be at least partially secured to structural support member 28 via inner liner 18 and/or outer jacket 24. For example, structural frame 70 may not be directly coupled to structural support member 28 or may not be in direct contact (e.g., abutting contact) with structural support member 28, although the two members may be in the same radial layer of catheter 10. In an example, a proximal portion of structural frame 70 and/or flexible membrane 48 may be positioned adjacent to structural support member 28 over inner liner 18, and outer jacket 24 may be positioned over structural support member 28, flexible membrane 48, and/or structural frame 70. Outer jacket 24 may be heat shrunk over the two members 20, 28 such that outer jacket 24 secures both expandable member 20 and structural support member 28 in place relative to inner liner 18. In some such examples, but not all such examples, flexible membrane 48 may be a distal extension of inner liner 18 and/or outer jacket 24.

For example, at least a portion of proximal section 40 (e.g., flexible membrane 48 and/or structural frame 70) of expandable member 20 may be positioned between inner liner 18 and outer jacket 24. One or both of inner liner 18 or outer jacket 24 may extend over the entire length of expandable member 20 or may extend over only a portion of the axial length of expandable member 20. In the example shown in FIG. 2, a proximal portion of flexible membrane 48 is positioned between the braided frame 70 of expandable member 20 and a distal portion of outer jacket 24 to form a continuous (e.g., seamless) catheter tip 60. In some examples, flexible membrane 48 may include a distal portion of inner liner 18 extending over only part of the length of expandable member 20 leaving portions of expandable member 20 exposed to inner lumen 26C. The exposed portions of expandable member 20 may provide better engagement with a thrombus and/or prevent distal migration of thrombus from catheter 10 due to the texture of expandable member 20 or direct electrostatic engagement with expandable member 20, as described above.

In some examples, both inner liner 18 and outer jacket 24 terminate proximal to a distal end of expandable member 20. In other examples, inner liner 18 and outer jacket 24 can have other arrangements relative to expandable member 20.

In some examples, elongated body 12 may include one or more radiopaque markers, such as marker band 38, which may help a clinician determine the positioning of catheter 10 relative to a target treatment site. For example, one or more radiopaque marker(s) 38 may be embedded within elongated body 12.

FIGS. 3A and 3B are conceptual side views of the example catheter 10 of FIGS. 1 and 2. As shown in FIG. 3A, when expandable member 20 is in a contracted configuration, ring 46 defines an axial length L and a compressed diameter d, wherein, in some examples, the compressed diameter d is larger than the axial length L. In the example of FIG. 3A, but not in all examples, compressed diameter d of expandable ring 46 is less than the diameter of elongated body 12 (as measured across a cross-section taken transverse to longitudinal axis 22), such that proximal section 40 of expandable member 20 defines a tapered or conical section of catheter 10, or such that expandable member 20 tapers in a distal direction.

Ring 46, and by extension, expandable member 20, is configured to expand radially outward from a compressed or contracted configuration (FIG. 3A) to a deployed or expanded configuration (FIG. 3B) in response to electrical energy applied to the expandable ring 46 from energy source 50 to ring 46 via electrical conductor 52.

Electrical conductor 52 is formed from any suitable electrically conductive material, which can be insulated from other parts of elongated body 12 along its length. In some examples, electrical conductor 52 comprises an electrically conductive wire, such as a copper, silver, and/or gold wire, surrounded by an electrically insulative material, such as polyamide. In some examples, electrical conductor 52 is part of structural support member 28 of elongated body 12 and/or structural frame 70 of expandable member 20. For example, in examples in which structural support member 28 and/or structural frame 70 includes a braided structure (e.g., a mixed-wire braid), electrical conductor 52 may include a conductive wire woven into mixed-wire braid. As another example, such as the example shown in FIGS. 1 and 2, elongated body 12 includes a coiled structural support member 28, and electrical conductor 52 includes a coiled wire interleaved with the coiled structural support member 28. As further shown in FIG. 2, structural frame 70 of expandable member 20 includes a braided structure, and a distal portion of electrical conductor 52 is braided into structural frame 70. In other examples, electrical conductor 52 may include a coiled wire that functions as the coiled structural support member of elongated body 12.

In some examples, catheter 10 includes electrical switch 44 having a user-input mechanism (e.g., a button, slider, lever, toggle, wheel, etc.) disposed at the proximal portion 16A of the elongated body 12 (e.g., on handle 14 of FIG. 1). During use of catheter 10, a clinician may actuate the user-input mechanism to close the electrical switch 44, thereby completing a circuit from energy source 50 (e.g., a battery, capacitor, electrical outlet, etc.), through electrical conductor 52, and into expandable ring 46. Expandable ring resistively heats and undergoes ohmic expansion to convert expandable member 20 from the contracted configuration shown in FIG. 3A to the expanded configuration shown in FIG. 3B. In the expanded configuration of FIG. 3B, expandable ring 46 defines an expanded outer diameter D which is larger than axial length L.

FIGS. 4A-4D are side elevation views of example rings and illustrate example shapes for expandable ring 46 of catheter 10 of FIG. 1. In any of the examples of FIGS. 4A-4D, the expandable rings may include any suitable structure, such as, but not limited to, solid metal structure, a braided-wire structure, a laser-cut-stent structure, or a combination thereof.

Figure 4A:
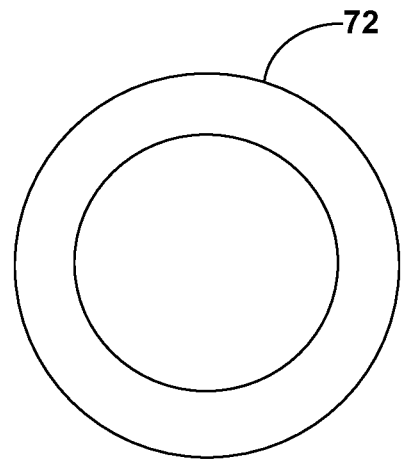
FIGS. 4A-4D are side elevation views of example expandable rings.
Figure 4B:
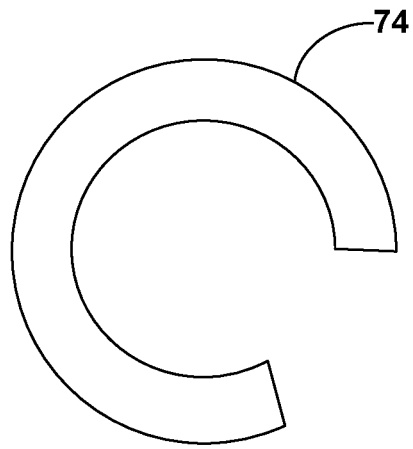
Figure 4C:
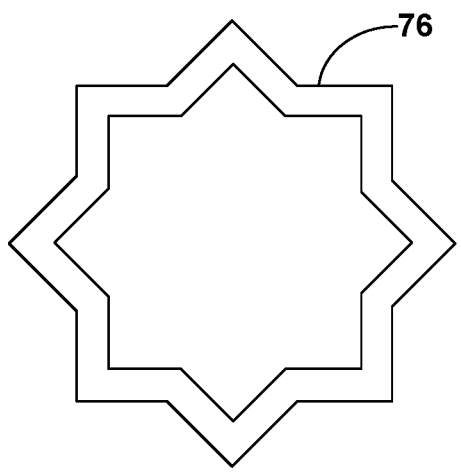
Figure 4D:
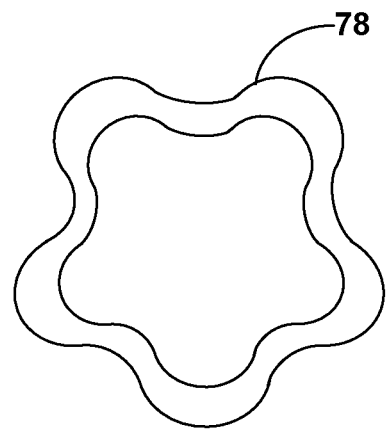

FIG. 4A depicts example expandable ring 72, which has a closed ring shape. An outer perimeter of ring 72 defines a complete circumference of a circle. FIG. 4B depicts another example expandable ring 74, which is a partial ring (also referred to as an open ring). An outer perimeter of expandable ring 74 defines a majority of the circumference (e.g., more than 50%, such as 60% to 95%, or about 75% to 90%) of a circle, but not a complete circumference of a circle.

Example expandable rings 76, 78, of FIGS. 4C and 4D, respectively, include geometric shapes that are non-circular in cross-section. For example, the outer perimeter of expandable ring 76 of FIG. 4C includes a geometric shape formed by undulating (e.g., zig-zagging) straight lines. Ring 78 of FIG. 4D includes an outer perimeter having a geometric shape formed by undulating (e.g., sinusoidal) curved lines. Ring 78 has a pleated-ring shape or flower-petal shape in cross-section, wherein an outer surface of ring 46 varies in radius and curves in and out (relative to longitudinal axis 22). In some examples of FIGS. 4C and/or 4D, expandable rings 76, 78 may be configured to fold radially inward at a plurality of points around the outer circumference while the expandable ring is in a contracted configuration, and then may expand into a circular or more-circular geometric shape when the expandable ring is in an expanded configuration. Although rings 76, 78 are shown as closed rings, in other examples, ring 76 and/or ring 78 may be partial rings.

Figure 5:
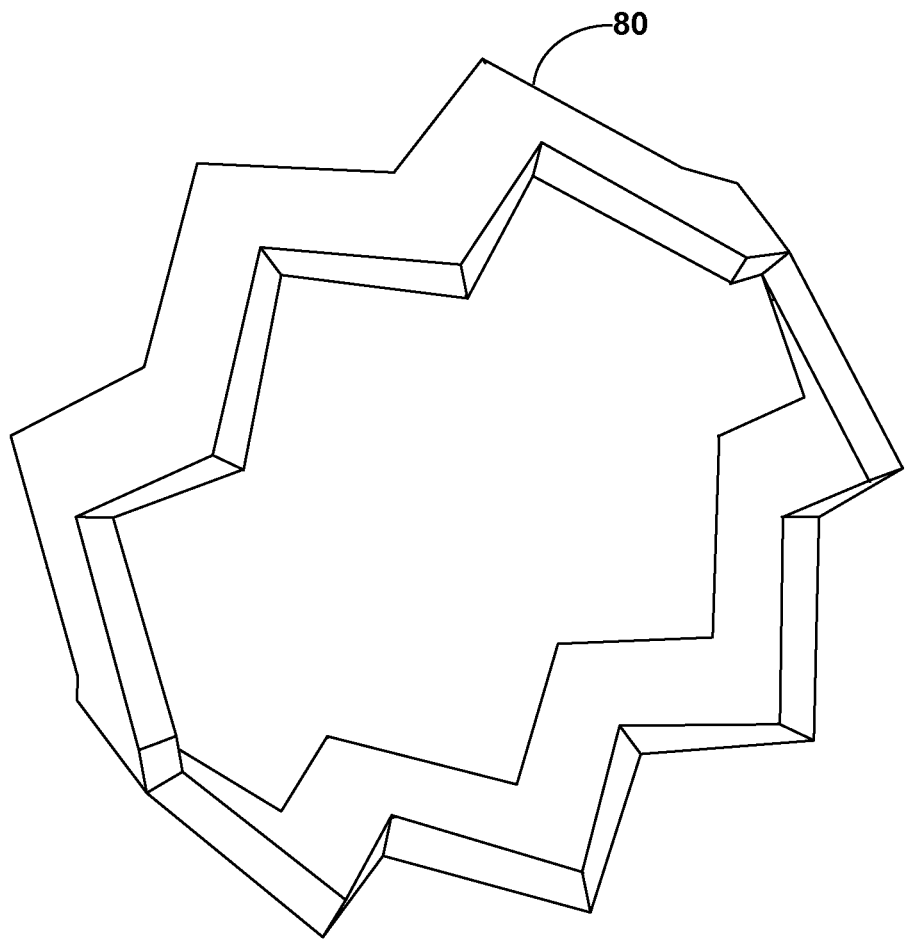
FIG. 5 is a perspective view depicting another example expandable ring.

FIGS. 4C and 4D illustrate example rings that have outer perimeters that vary in in a radial direction, e.g., defines surfaces that vary in distance relative to longitudinal axis 22. Instead of or in addition to the radial direction, in some examples, the proximal and/or distal edges of an expandable ring may undulate or have another shape. FIG. 5 is a perspective view of another example expandable ring 80, which may be an example of expandable ring 46 of catheter 10 of FIG. 1. Expandable ring 80 may include any suitable structure, such as, but not limited to, a solid metal structure, a braided-wire structure, a laser-cut-stent structure, or a combination thereof. As shown in FIG. 5, expandable ring 80 may include a geometric shape having a circular cross-section (e.g., having a constant radius), but may oscillate, undulate, or vary along an axial direction (parallel to longitudinal axis 22). For example, an outer surface of expandable ring 80 may form a zig-zag shape or sinusoidal shape as it wraps or extends around the circumference of expandable ring 46. The various example shapes and features of expandable members of this disclosure are not mutually exclusive. For example, the shape of expandable member 80 of FIG. 5 may be used in combination with any or all of the shapes of expandable members 72-78 of FIGS. 4A-4D.

Figure 6:
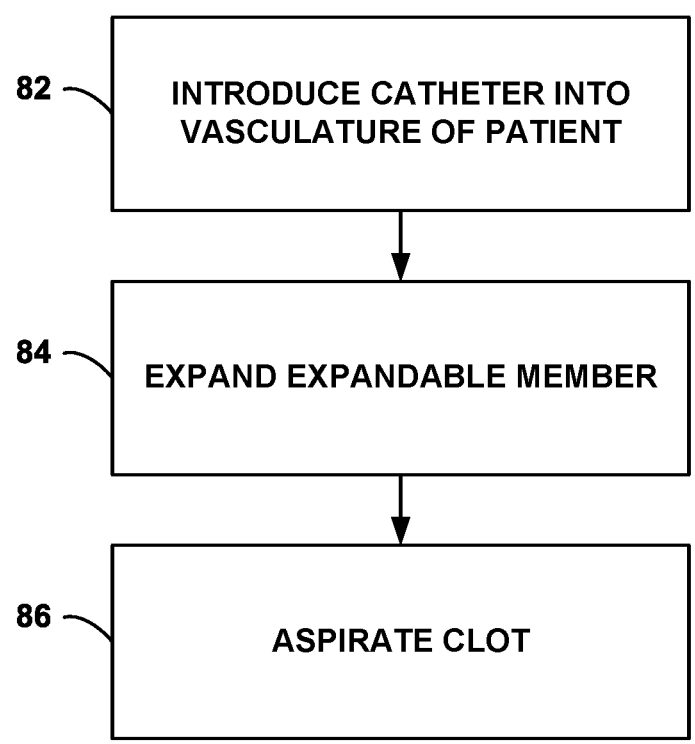
FIG. 6 is a flow diagram of an example method of using a catheter.

FIG. 6 is a flow diagram of an example method of aspiration using catheter 10 of FIGS. 1 and 2. The techniques of FIG. 5 include inserting catheter 10 into vasculature of the patient (82), expanding expandable member 20 in the vasculature of the patient (84), and aspirating a thrombus (86). In some examples, the techniques described herein include removing catheter 10 from the vasculature of the patient once the procedure is complete.

A clinician may insert catheter 10 into vasculature of a patient (82) by initially introducing a guidewire, guide catheter, or another guide member into the vasculature of the patient to a target treatment site. Elongated body 12 may then be introduced over the guidewire and advanced to the target treatment site. Additionally, or alternatively, catheter 10 may be introduced into vasculature of a patient with the aid of a guide catheter. For example, the guide catheter may be initially introduced into vasculature of a patient and positioned adjacent a target treatment site. Catheter 10 may then be introduced through an inner lumen of the guide catheter.

Once within the vasculature, expandable member 20 may be expanded in the vasculature (84) by at least delivering an electrical current to ring 46 to cause ring 46 to expand radially outwards. For example, a clinician may actuate a user-input mechanism to close an electrical switch 44, thereby transferring electrical power from a power source 50 to ring 46 via electrical conductor 52. Ring 46 resistively heats and expands according to the thermal properties of its composing materials, thereby causing expandable member 20 to expand, and widening distal mouth 62 to better engage with a thrombus.

The technique of FIG. 5 also includes applying a suction force to inner lumen 26 of catheter 10 to remove the thrombus from the vasculature (86). For example, once distal tip or portion 60 of catheter 10 is positioned proximate to a thrombus, a clinician may actuate a suction source to apply a suction force to lumen 26. The suction source can comprise a pump, such as a direct-acting pump (e.g., a peristaltic pump, or a lobe, vane, gear, or piston pump, or other suitable pumps of this type) or an indirect-acting pump (e.g., a vacuum pump, which creates a partial vacuum in an evacuation volume fluidically coupled to the liquid to be displaced).

In some examples, the suction force applied to inner lumen 26 of catheter 10 is varied over time, referring to herein as cyclical aspiration. As discussed above, during this cyclical aspiration, expandable member 20 may axially compress and expand in response to the varying suction force. Once the aspiration procedure is complete, the clinician may open electrical switch 44, thereby allowing expandable member 20 to self-contract back to a contracted configuration, wherein catheter 10 may then be removed from the vasculature of the patient.

Various aspects of the disclosure have been described. These and other aspects are within the scope of the following claims.

What is claimed is:

1. A catheter comprising:
   an elongated body comprising a proximal body portion and a distal body portion;
   an expandable member located at the distal body portion, the expandable member defining a distal section and a proximal section between the elongated body and the distal section, wherein the expandable member comprises:
   a flexible membrane; and
   an expandable ring or partial ring located at the distal section of the expandable member, the expandable ring or partial ring being configured to expand radially outward in response to electrical energy applied to the expandable ring or partial ring; and
   an electrical conductor extending along the elongated body, the electrical conductor configured to deliver the electrical energy from an energy source to the expandable ring or partial ring,
   wherein the proximal section of the expandable member is not configured to resistively heat in response to the electrical energy delivered from the electrical conductor.

2. The catheter of claim 1, wherein the expandable member is configured to expand radially outward from a compressed configuration to a deployed configuration in response to the electrical energy applied to the expandable ring or partial ring.

3. The catheter of claim 1,
   wherein the expandable ring or partial ring defines an axial length and a compressed diameter, and
   wherein the compressed diameter is larger than the axial length.

4. The catheter of claim 1, wherein the expandable ring or partial ring comprises nitinol or a 50:50 nickel-titanium alloy.

5. The catheter of claim 1,
   wherein the elongated body comprises a braided structural support member, and
   wherein the electrical conductor is woven into the braided structural support member.

6. The catheter of claim 1,
   wherein the elongated body comprises a coiled structural support member, and
   wherein the electrical conductor comprises a coiled wire interleaved with the coiled structural support member.

7. The catheter of claim 1, wherein the elongated body comprises a coiled structural support member comprising the electrical conductor.

8. The catheter of claim 1,
   wherein the expandable ring or partial ring comprises a nitinol frame defining a plurality of pores, and
   wherein the expandable ring or partial ring is configured to resistively heat in response to receiving the electrical energy.

9. The catheter of claim 8, wherein the nitinol frame comprises a plurality of interwoven nitinol wires.

10. The catheter of claim 1, wherein the membrane comprises a polymer fabric disposed around the expandable ring or partial ring.

11. The catheter of claim 10, wherein the polymer fabric comprises silicone, polyethylene terephthalate (PET), or expanded polytetrafluoroethylene (e-PTFE).

12. The catheter of claim 1, wherein the elongated body comprises:
   an inner liner;
   a structural support member;
   an outer jacket; and
   a radiopaque marker band,
   wherein the structural support member is positioned between the outer jacket and the inner liner.

13. The catheter of claim 1, further comprising an electrical switch disposed at the proximal portion of the elongated body, the electrical switch being configured to apply the electrical energy to the expandable ring or partial ring when the electrical switch is closed.

14. The catheter of claim 1, wherein the expandable member defines a cylindrical tube while in a deployed configuration.

15. The catheter of claim 1, wherein the expandable member tapers in a distal direction while the expandable member is in a compressed configuration.

16. The catheter of claim 1, wherein the expandable ring or partial ring is disposed at a distal-most end of the expandable member.

17. A method of aspirating a clot, comprising:

distally advancing a catheter within a vasculature of a patient toward the clot, wherein the catheter comprises an expandable member comprising a flexible membrane and an expandable ring or partial ring, the expandable member defining a distal section and a proximal section between the elongated body and the distal section;

closing an electrical switch to apply electrical energy via an electrical conductor to the expandable ring or partial ring to cause the expandable member to expand radially outward wherein the proximal section of the expandable member is not configured to resistively heat in response to the electrical energy delivered from the electrical conductor;

actuating a suction force to aspirate the clot;

opening the electrical switch to cause the expandable member to contract radially inward; and proximally withdrawing the catheter from the vasculature of the patient.

18. The method of claim 17, wherein the expandable ring or partial ring comprises a nitinol frame defining a plurality of pores, and wherein the expandable ring or partial ring is configured to resistively heat in response to receiving the electrical energy.

19. A system comprising:
an energy source; and
a catheter comprising:
an elongated body comprising a proximal body portion and a distal body portion; and
an expandable member located at the distal body portion, wherein the expandable member is configured to expand radially outward, the expandable member defining a distal section and a proximal section between the elongated body and the distal section, and wherein the expandable member comprises:
a flexible membrane; and
an expandable ring or partial ring located at a distal section of the expandable member, the expandable ring or partial ring being configured to expand radially outward in response to electrical energy applied from the energy source to the expandable ring or partial ring; and
an electrical conductor extending along the elongated body, the electrical conductor configured to deliver the electrical energy from an energy source to the expandable ring or partial ring,
wherein the proximal section of the expandable member is not configured to resistively heat in response to the electrical energy delivered from the electrical conductor.

20. The catheter of claim 1, wherein the proximal section further comprises a metal frame that is not electrically coupled to the electrical conductor.

\* \* \* \* \*